(12) United States Patent
Zhong et al.

(10) Patent No.: US 9,149,392 B2
(45) Date of Patent: Oct. 6, 2015

(54) CASTING APPARATUS

(71) Applicants: Bing-Tang Zhong, Houston, TX (US); Ping-Chung Chung, Xin Zhu (TW); Yueh-Lin Chung, Xin Zhu (TW)

(72) Inventors: Bing-Tang Zhong, Houston, TX (US); Ping-Chung Chung, Xin Zhu (TW); Yueh-Lin Chung, Xin Zhu (TW)

(*) Notice: Subject to any disclaimer, the term of this patent is extended or adjusted under 35 U.S.C. 154(b) by 0 days.

(21) Appl. No.: 14/055,258

(22) Filed: Oct. 16, 2013

(65) Prior Publication Data

US 2014/0257157 A1    Sep. 11, 2014

Related U.S. Application Data

(60) Provisional application No. 61/720,376, filed on Oct. 30, 2012.

(51) Int. Cl.
| A61F 5/37 | (2006.01) |
| A61B 19/00 | (2006.01) |
| A61F 5/00 | (2006.01) |
| A61F 13/06 | (2006.01) |
| A61L 15/00 | (2006.01) |
| A61F 13/04 | (2006.01) |
| A61F 13/02 | (2006.01) |
| A61F 13/00 | (2006.01) |
| A61F 5/01 | (2006.01) |

(52) U.S. Cl.
CPC ............. *A61F 13/041* (2013.01); *A61F 5/00* (2013.01); *A61F 5/01* (2013.01); *A61F 13/00* (2013.01); *A61F 13/02* (2013.01); *A61F 13/0273* (2013.01); *A61F 13/04* (2013.01)

(58) Field of Classification Search
CPC ............ A61F 5/00; A61F 5/01; A61F 13/00; A61F 13/00361; A61F 13/02; A61F 13/0273; A61F 13/04; A61F 13/041
USPC ................ 602/3, 5–8, 32–36, 60–66, 75–76; 128/845, 869, 877–878, 882
See application file for complete search history.

(56) References Cited

U.S. PATENT DOCUMENTS 5,899,425 A * 5/1999 Corey, Jr. et al. .......... 248/276.1

* cited by examiner

*Primary Examiner* — Alireza Nia
*Assistant Examiner* — Brandon L Jackson
(74) *Attorney, Agent, or Firm* — Nick A Nichols, Jr.

(57) ABSTRACT

In a casting apparatus for external skeletal and joint fixation, a plurality of articulated segments may comprise a plurality of cuboid members threaded on a continuous cord having distal ends connected to actuators. The cuboid members may be disposed between guide members threaded on the cord. Actuation of the actuators applies a tension force to the cord, thereby compressing the cuboid members together to form rigid cuboid segments and maintain the casting apparatus in a rigid configuration for skeletal and joint fixation.

8 Claims, 4 Drawing Sheets

CASTING APPARATUS

CROSS-REFERENCE TO RELATED APPLICATION

This application claims the benefit of U.S. Provisional Application Ser. No. 61/720,376, filed Oct. 30, 2012, which application is incorporated herein in its entirety by reference.

BACKGROUND

The present invention relates generally to the field of casting apparatus, and more particularly to a casting apparatus forming a rigid structure for application in skeletal and joint fixation.

In clinical practice, there are many conditions and circumstances, such as fractures and dislocations of bones and joints, injuries of muscles, tendons, fasciae and ligaments, correction of congenital and acquired deformities, etc., in which the involved skeletal system has to be fixed for treatment. Plaster of paris (gypsum plaster) has been used as casting material for skeletal and joint fixation for more than one hundred years and is still the standard casting material in many countries. But it is not without drawbacks, such as heavy weight, water intolerance, etc. In recent years, synthetic resin (polyurethane resin, etc.) has been used widely and has become part of the established orthopedic practice in most developed countries. Although resin impregnated splinting bandages have many advantages over traditional based materials, they still have some drawbacks. Typically, synthetic splints are created from a resin impregnated fabric contained within a moisture impervious sleeve prior to use. In use, the resin impregnated fabric is wetted and then applied to the body part requiring a splint. A synthetic splint thus requires an activator, may irritate the skin and cause an allergic reaction. Both the plaster-of-paris and the synthetic resin casts require a substantial period of time for the cast to set and harden, require multiple steps to prepare and can be difficult to apply. In addition, these types of casts are removed by cutting them off the patient and discarded, and thereby adding to the pollution of the environment.

The casting apparatus disclosed and described herein eliminates the disadvantages of plaster of paris and synthetic resin casting material and methods. Moreover, the casting apparatus disclosed and described herein may be used many times, hence there is no waste and trash to pollute the environment and energy and water are conserved by eliminating the multi-step preparation process required by the plaster of paris and synthetic casting methods.

SUMMARY

In a casting apparatus for skeletal and joint fixation, the casting apparatus may comprise a plurality of cuboid members threaded on a continuous cable, such as a wire or chain. The distal ends of the cable may be connected to an actuator. The cuboid members may be disposed between guide members threaded on the cable to form cuboid segments. The cuboid segments may be of varying lengths. Actuation of the actuator may apply a tension force on the cable and compress the cuboid members between guide members, thereby forming rigid cuboid segments and maintaining the casting apparatus in a rigid configuration.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 12 is partial sectional elevation view of another embodiment of a casting apparatus.

DETAILED DESCRIPTION

Figure 1:
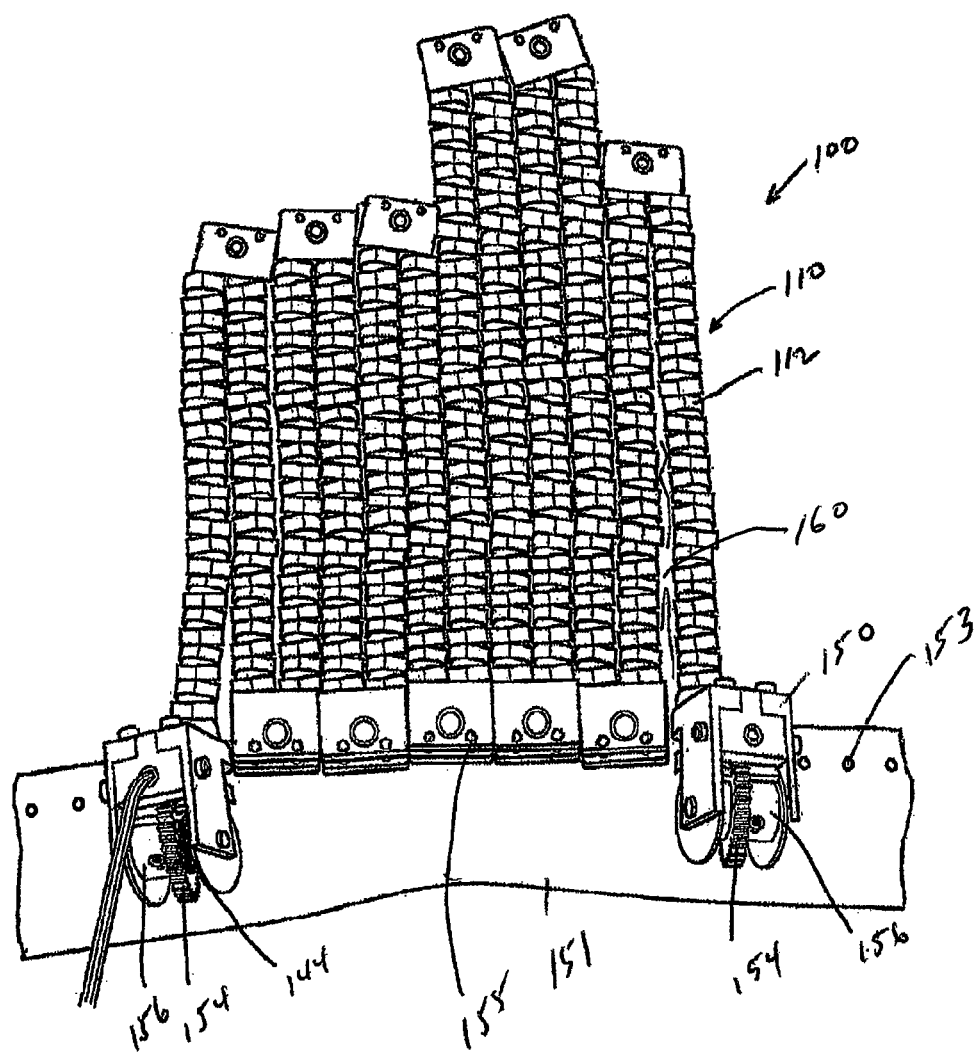
FIG. 1 is a partial sectional perspective view of a casting apparatus.

Referring first to FIG. 1, a casting apparatus for skeletal and joint fixation is generally identified by the reference numeral 100. The casting apparatus 100 may include a plurality of articulated cuboid segments 110. The segments 110 may comprise a plurality of cuboid members 112 threaded on a continuous chain 114 or similar thread-like cord, such as a cable or wire or the like.

Figure 2:
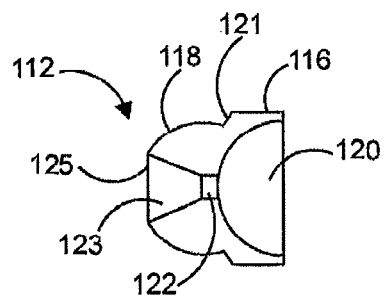
FIG. 2 is a section view of a cuboid member of the casting apparatus shown in FIG. 1.

Referring now to FIG. 2, the cuboid members 112 may include a lower portion 116 and an upper portion 118. The upper portion 118 defines a substantially semi-spherical or dome-like shape. The top of the upper portion 118 may be truncated along a transverse plane perpendicular to the rotational axis of the cuboid member 112.

The lower portion 116 of the cuboid member 112 may include a socket or cavity 120 configured to receive the upper portion 118 of a cuboid member 112. The outer surface of the lower portion 116 of the cuboid member 112 may define a substantially cylindrical shape or other suitable shape. The outer surface of the lower portion 116 of the cuboid member 112 may terminate at a circumferential transition surface 121 that tapers upwardly and inwardly to the lower circumferential edge of the upper portion 118 of the cuboid member 112.

Figure 3:
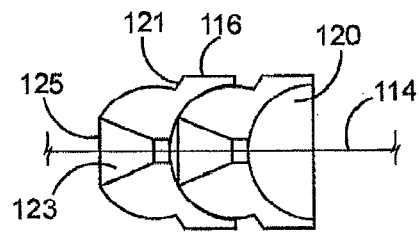
FIG. 3 is a fragmentary section view of cuboid members of the casting apparatus shown in FIG. 1 in cooperating interfacing contact.
Figure 4:
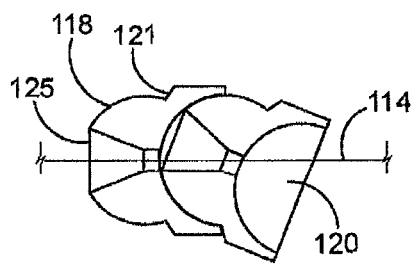
FIG. 4 is a fragmentary section view illustrating relative motion between cuboid members of the casting apparatus shown in FIG. 1.

While the cuboid members 112 shown in FIGS. 2-4 are substantially the same in size and shape, it is understood that the cuboid members 112 may be of different sizes and shapes. For example, the axial lengths of the lower and upper portions 116 and 118 of the cuboid members 112 may vary. The range of articulated movement of the cuboid segments 110 may be extended by arranging cuboid members 112 of different sizes and shapes on the chain 114 to form a cuboid segment 110.

Referring still to FIG. 2, the upper portion 116 of the cuboid member 112 may be provided with a cone-like passageway 123 that tapers circumferentially inwardly from an edge 125 at the truncated end of the upper portion 116. The passageway 123 terminates at an opening 122 providing access to the cavity 120 of the cuboid members 112.

Referring now to FIGS. 3 and 4, a plurality of cuboid members 112 may be threaded on the chain 114 to form a cuboid segment 110. FIG. 3 illustrates the interface between adjacent cuboid members 112 depicting the upper portion 118 of a cuboid member 112 received within the cavity 120 of a cuboid member 112. Cuboid members 112 may be threaded on the chain 114 to form cuboid segments 110 of various lengths. The dome and socket interface between the cuboid members 112 permits adjoining cuboid members 112 to move relative to each other as shown in FIG. 4.

Figure 5:
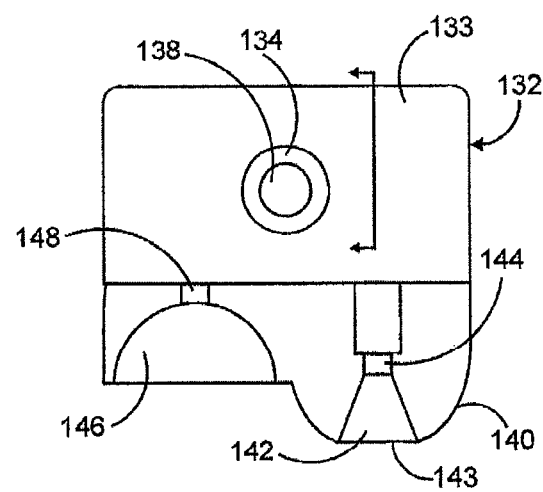
FIG. 5 is a section view of a guide member of the casting apparatus shown in FIG. 1.
Figure 6:
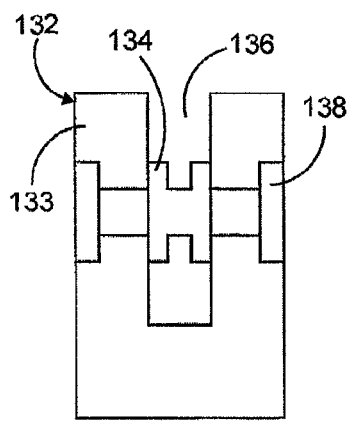
FIG. 6 is a section view taken along line 6-6 of FIG. 5.

Referring now to FIGS. 1-7 collectively, the casting apparatus 100 may include a plurality of cuboid segments 110 formed by threading cuboid members 112 on the chain 114 to form the desired length for each cuboid segment 110. A guide 132 defining a distal end of a cuboid segment 110 may be threaded on the chain 114. The guide 132 may include an upper portion formed by spaced apart tabs 133 defining a slot 136 therebetween, as best shown in FIG. 6. A transverse shaft 138 supported by the tabs 133 extends across the slot 136. A guide roller 134 rotatably mounted on the shaft 138 may be disposed between the tabs 133.

Figure 7:
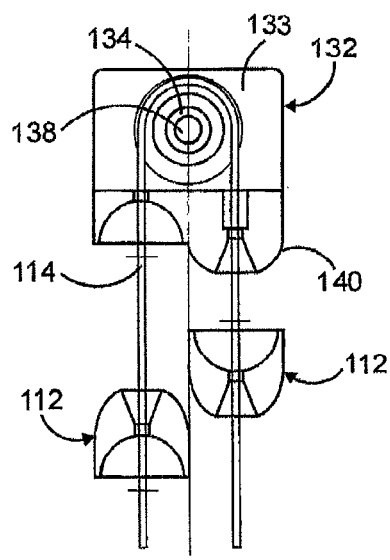
FIG. 7 is an exploded fragmentary section view illustrating the interface between a guide member and cuboid members of the casting apparatus shown in FIG. 1.

Referring now specifically to FIG. 5, the lower portion of the guide 132 may include a semi-spherical protrusion 140 configured to be received in a cavity 120 of a cuboid member 112. A passageway 142 extends from the lower end 143 of the protrusion 140 to an axial opening 144 extending through the guide 132 to the base 145 of the slot 136. The opening 144 opens into the slot 136 of the guide 132. The guide 132 may further include a socket 146 configured to receive the upper semi-spherical portion 118 of a cuboid 112. An opening 148 provides access between the socket 146 and the slot 136 of the guided 132. The chain 114 may be threaded through the opening 144 of the protrusion 140 over the guide roller 134 and through the opening 148 of the socket 146 of the guide 132, as shown in FIG. 7. The openings 144 and 148 are laterally spaced apart and aligned in a vertical plane passing through the center of the openings 144 and 148. Additional cuboid members 112 may be threaded on the chain 114 to form the next segment 110. The process may be repeated to form additional segments 110 to create the desired size and shape of the casting apparatus 100.

Referring again to FIG. 1, the casting apparatus 100, for purposes of illustration and not by way of limitation, comprises twelve articulated cuboid segments 110 arranged in segment pairs of different lengths. Each segment 110 comprises a plurality of cuboid members 112 threaded on the chain 114 between guides 132. The guides 132 define the distal ends of the cuboid segments 110. The distal ends of the continuous chain 114 may be secured to a respective actuator 150. For example, the actuator 150 may comprise a worm drive having a worm screw 152 in cooperative engagement with a worm wheel 154. The worm wheel 154 is fixed to a transverse shaft 156 rotatably supported by the actuator 150. The distal ends of the chain 114 are fixed to the transverse shaft 156 of a respective actuator 150. Actuation of the actuator 150 by turning the worm screw 152 rotates the worm wheel 154 and thereby winds the chain 114 on the shaft 156.

The assembled cuboid segments 110 may be arranged in a substantially planar configuration, as shown in FIG. 1. The relative relationship and spacing of the cuboid segments 110 may be maintained by securing the cuboid segments 110 and actuators 150 to a strap 151. The strap 151 may be fabricated of a flexible material and include a plurality of holes 153 spaced along an edge thereof. The guides 132 may include holes 155 that may be aligned with the holes 153 in the strap 151. A fastener, such as a bolt or the like, may be inserted through the aligned holes 153 and 155 to secure the guides 132 and thereby an end of the cuboid segments 110 to the strap 151. The actuators 150 may be secured to the strap 151 in a similar manner. The cuboid segments 110 may be slightly spaced apart from each other, as best shown in FIG. 12.

Figure 13:
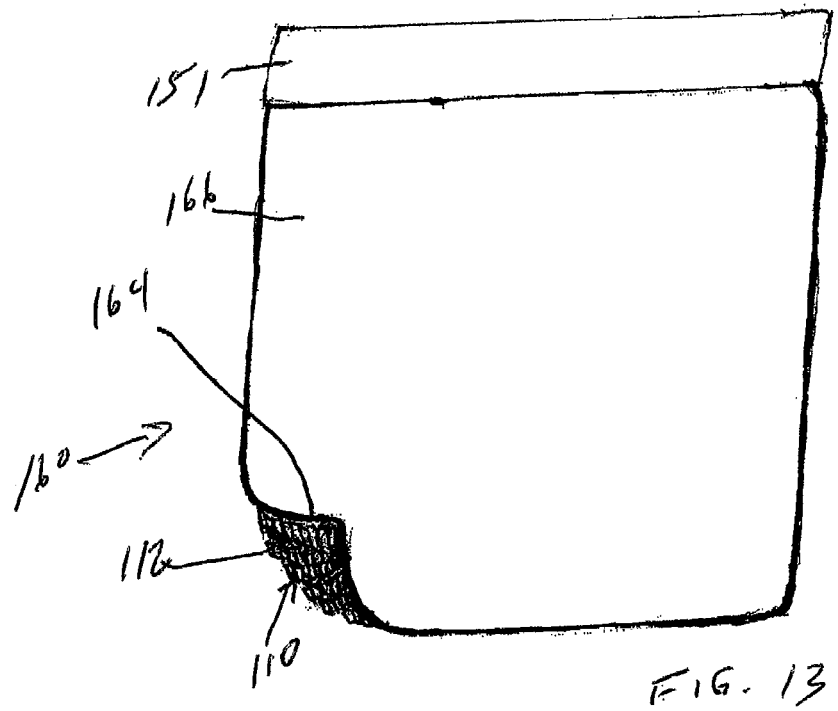
FIG. 13 is a plan view of a backing applied to the casting apparatus shown in FIG. 12.
Figure 14:
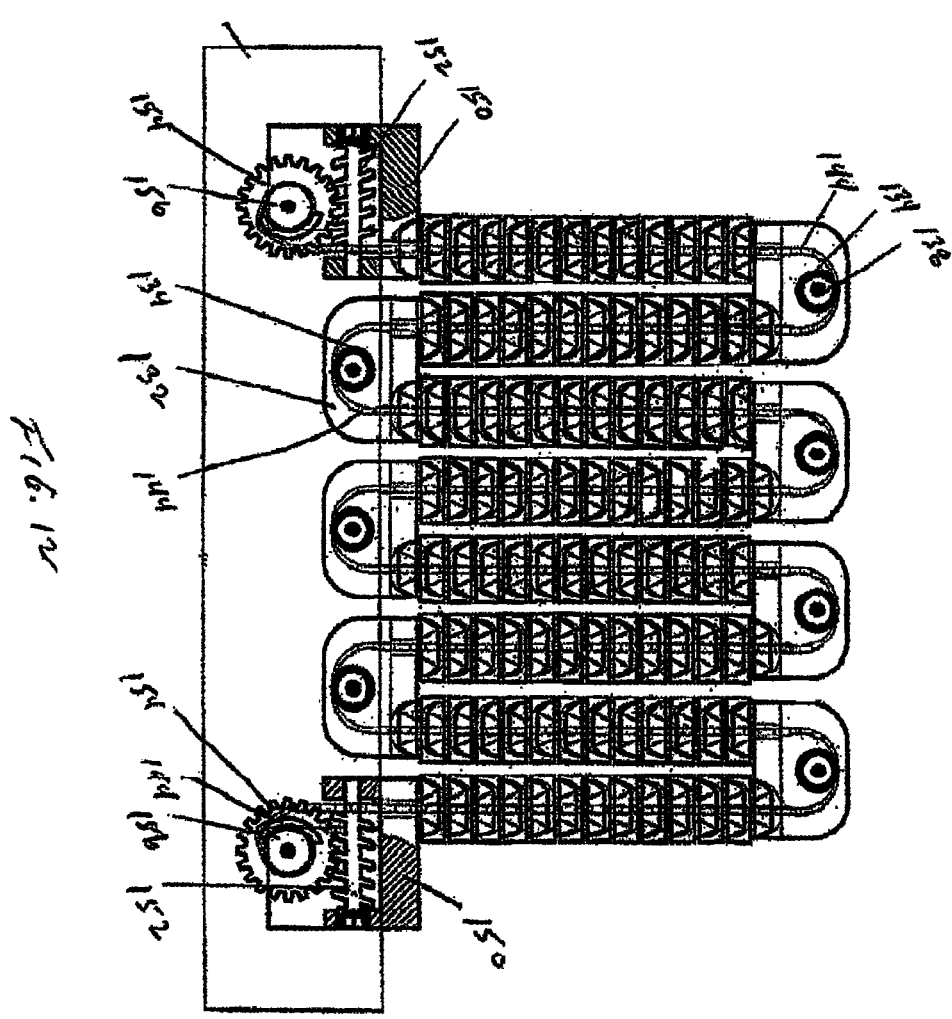

The configuration and relative spacing of the segments 110 may further be facilitated by an elastic backing 160, shown in FIG. 13. The backing 160 may include an adhesive side 164 and a fastener side 166. The cuboid segments 110 and cuboid members 112 may be fixed to the adhesive side 164 of the backing 160. The fastener side 166 of the backing 160 may comprise a hook and loop fastener, such as Velcro and the like. The backing 160 is flexible and stretchable so that the cuboid segments 110 may be manipulated to a configuration to fit about a limb fracture or other skeletal system requiring external fixation.

Figure 8:
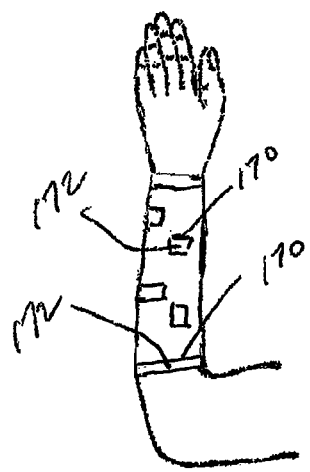
FIG. 8 is a side elevation view of a forearm prepared for application of a casting apparatus.
Figure 9:
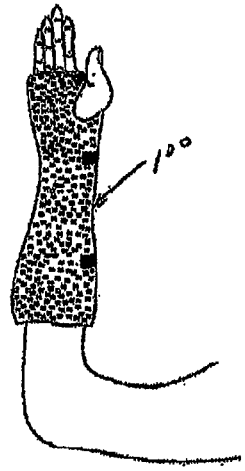
FIG. 9 is side elevation view of a casting apparatus applied to a forearm.

Referring now to FIGS. 8 and 9, collectively, the casting apparatus 100 is shown fixed about a patient's forearm. Adhesive strips or patches 170, shown in FIG. 8, are first attached to the forearm with the adhesive side against the skin and the fastener side 172 facing outward. The casting apparatus 100 may be applied to the forearm by wrapping it about the forearm so that the fastener side 166 of the elastic backing 160 adheres to the fastener side 172 of the adhesive strips or patches 170 to hold the casting apparatus 100 in position. The cuboid segments 110 may be manipulated to fit the casting apparatus 100 about the shape of the forearm. Actuation of the actuator 150 applies a pulling or tension force to the chain 114, thereby compressing the cuboid members 112 together to form rigid cuboid segments 110 and maintain the casting apparatus 100 in a rigid configuration about the forearm. The casting apparatus 100 may be wrapped with an elastic bandage, such as an Ace bandage, if desired, particularly if the casting apparatus 100 is to provide external skeletal and joint fixation for longer than a short period of time.

Figure 10:
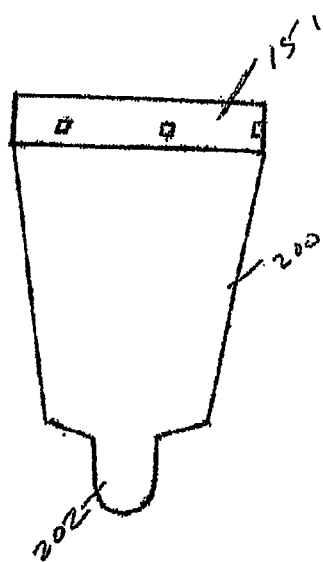
FIG. 10 is a side elevation view of a casting apparatus configured for application to a leg.
Figure 11:
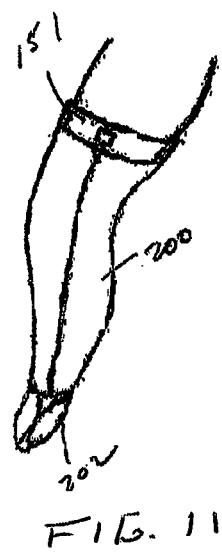
FIG. 11 is a front elevation view of the casting apparatus shown in FIG. 10 applied to a leg.

It is understood that the number of articulated segments 110 that may form the casting apparatus 100 is not limited to the number of segments 110 shown in FIG. 1. The casting apparatus 100 may include multiple articulated segments 110 of the same or different lengths to form casting apparatus 100 of various sizes and shapes. For example, a casting apparatus 200 configured to be applied about a leg is shown in FIGS. 10 and 11. The casting apparatus 200 may include a foot portion 202 that may wrap about a foot as shown in FIG. 11.

While a preferred embodiment of the invention has been shown and described, other and further embodiments of the invention may be devised without departing from the basic scope thereof, and the scope thereof is determined by the claims which follow.

The invention claimed is:

1. A casting apparatus comprising:
   a) a first articulated cuboid segment and a second cuboid segment, each of said first and second cuboid segments having a proximal end and a distal end;
   b) a plurality of intermediate articulated cuboid segments operatively connected between said first cuboid segment and said second cuboid segment, each of said intermediate cuboid segments extending substantially parallel to said first and second cuboid segments and having a proximal end and a distal end;

c) a first actuator operatively connected to said proximal end of said first cuboid segment and a second actuator operatively connected to said proximal end of said second cuboid segment, wherein said first and second actuators are spaced apart from each other and fixedly secured to an elongated flexible strap;

d) a continuous cord threaded through said first and second cuboid segments and said intermediate cuboid segments, said cord having a first distal end connected to said first actuator and a second distal end connected to said second actuator;

e) a first set of guide members threaded on said cord defining the distal ends of said cuboid segments;

f) a second set of guide members threaded on said cord fixedly secured to said elongated flexible strap between said first and second actuators, said proximal ends of said intermediate cuboid segments being in frictional engagement with a guide member of said second set of guide members; and g) wherein simultaneous or alternating actuation of said first and second actuators applies a tension force to said cord compressing said cuboid segments to maintain said cuboid segments in a rigid configuration.

2. The casting apparatus of claim 1 wherein each said cuboid segments comprise a plurality of cuboid members, wherein said cuboid members include a semi-spherical end having a convex surface and socket end having a concave surface, and wherein said cuboid members are threaded on said cord in interfacing frictional engagement.

3. The casting apparatus of claim 2 wherein said cuboid segments are fixed to an elastic backing, said backing having an adhesive side and a fastener side.

4. The casting apparatus of claim 3 wherein said fastener side of said backing comprises a hook and loop fastener.

5. The casting apparatus of claim 2 wherein each said cuboid members include a passageway extending said semi-spherical end.

6. The casting apparatus of claim 1 wherein said guide members include a roller supported on a transverse shaft in a slot defined between spaced apart upstanding walls of said guide members.

7. The casting apparatus of claim 6 wherein said guide members further include a protrusion and a socket, wherein said protrusion is sized for frictional engagement with said concave surface of a cuboid member and said socket is sized for frictional engagement with said convex surface of a cuboid member.

8. The casting apparatus of claim 1 wherein said actuators are worm drive actuators.

* * * * *